United States Patent [19]

Busch, Jr.

[11] Patent Number: 4,804,532
[45] Date of Patent: Feb. 14, 1989

[54] FACIAL COSMETIC POWDER CONTAINING CRYSTALLINE SILICA AND COLORS

[75] Inventor: Francis Busch, Jr., Southbury, Conn.

[73] Assignee: Laura Lupton Inc., Rowayton, Conn.

[21] Appl. No.: 905,630

[22] Filed: Sep. 9, 1986

[51] Int. Cl.[4] .................... A61K 7/035; A61K 7/021
[52] U.S. Cl. .......................................... 424/69; 424/63
[58] Field of Search ...................... 424/63, 69, 127; 514/770, 844; 106/482, 491

[56] References Cited

U.S. PATENT DOCUMENTS

| | | | |
|---|---|---|---|
| 3,978,207 | 8/1976 | Fotiu et al. | 424/63 |
| 4,403,963 | 9/1983 | Yoshida et al. | 427/407.1 X |
| 4,407,789 | 10/1983 | Eigen et al. | 424/69 |
| 4,659,562 | 4/1987 | Arraudeau et al. | 514/770 X |

FOREIGN PATENT DOCUMENTS

| | | | |
|---|---|---|---|
| 72906 | 5/1982 | Japan | 514/770 |
| 161213 | 7/1986 | Japan | 424/69 |

Primary Examiner—Ellis P. Robinson
Assistant Examiner—Susan S. Rucker

[57] ABSTRACT

A facial cosmetic powder having a coloring phase containing crystalline silica and coloring material and a diluent phase containing talc and a binding agent.

6 Claims, No Drawings

FACIAL COSMETIC POWDER CONTAINING CRYSTALLINE SILICA AND COLORS

CROSS REFERENCE TO COPENDING APPLICATION

The present application is related to copending application entitled FACIAL COSMETIC LIQUID CONTAINING CRYSTALLINE SILICA AND COLORS, Ser. No. 905,631 filed on even date herewith and owned by the assignee of the present application.

THE PRIOR ART

Certain foundation cosmetic creams are now described and sold as wrinkle smoothers and pore minimizers. One such cream employs 25 to 40 parts by weight of crystalline silica. This silica is employed because the cream is transparent and the refractive index and plate-like shape of the mineral permits the cream as applied to be indistinguishable from the skin itself, making lines and pores difficult to see. However, it is a characteristic of this cream that, when in place and viewed directly at an angle of ninety degrees, the wrinkles, lines and pores which lie underneath the foundation become visible. The silica itself is sold commercially by Malvern Minerals Company of Hot Springs National Park, Ark. under the brand name 1250 NOVACITE. It has an average particle size falling within the range of 7.3 to 12.9 microns and the particles have a characteristic plate like shape.

SUMMARY OF THE INVENTION

The present invention is directed toward a facial powder utilizing crystalline silica in much smaller parts by weight [1-3] which can be highly colored for use as a cake type make up or blush or which can be somewhat less colored as for example skin colored for use as a coating over the entire skin area. Whether used as a blush or as a facial coating, the covering power is such that wrinkles, lines and pores can be completely hidden.

In accordance with the principles of the invention, the face powder consists of a color producing phase and a diluent phase. These phases are produced separately and then combined, to produce the face powder in final form.

The color producing phase contains the color or colors to be used, {one or more conventional iron oxide colors with or without titanium dioxide}, and crystalline silica. These constituents are then processed through a high shear dispersion machine such as a hammer mill. The processing is continued until the colors are coated onto the silica which has a flat plate-like shape.

The diluent phase contains talc and a binding agent such as magnesium carbonate and/or bismuth oxychloride. Optionally, mica can be added.

The two phases are then mixed together until throughly blended. The final product, the face powder, contains 40-60 parts by weight of talc; 2-7 parts by weight of a binding agent; 1-3 parts by weight of crystaline silica; 5-15 parts by weight of mica [when used]; 1-3 parts by weight of titanium dioxide {when used}. The iron oxide color content can be increased or decreased as desired to produce skin colored or highly colored facial powder, but normally falls within the range of 0.5-10 parts by weight.

Different colors such as gold, peach, rose and blush, in various shades are obtained in known manner by mixing together different proportions of iron oxide color materials identified in the trade as russet, brown, yellow, red, and ultramarine blue, as well as titanium dioxide which, when used provides a white base.

The plate-like structure of the silica enables it to become a carrier of the coloring material which adheres thereto. The amount of coloring material suspended uniformly in a given weight of powder when the silica is used is substantially increased as compared to the amount of coloring material suspended uniformly in the same weight of powder when the conventional technique of using the oxides and stearates of zinc as the color carrier is used. As a result, the covering power of the powders in accordance with this invention is substantially increased, whereby the facial wrinkles, lines and pores of the user can be completely hidden when these powders are used. The coating on the skin does not cake or appear chalky.

SPECIFIC EXAMPLE

A typical cosmetic powder in accordance with the invention has the following formula:

| INGREDIENT | PARTS BY WEIGHT |
|---|---|
| coloring phase | |
| crystalline silica | 2.0 |
| iron oxide colors | 0.5 |
| titanium dioxide | 2.0 |
| diluent phase | |
| talc | 50.0 |
| magnesium carbonate | 5.0 |
| mica | 10.0 |
| bismuth oxychloride | 0.5 |

What is claimed is:

1. A facial cosmetic powder which when applied to the face of a user completely hides facial wrinkles, lines and pores without caking or appearing chalky, said powder comprising:
   a coloring phase containing crystalline silica and coloring material, said silica having a plate-like structure and an average particle size falling within the range of 7.3 to 12.9 microns; and
   a diluent phase containing talc and a binding agent, the coloring and diluent phases being thoroughly blended, the silica content falling within the range of 1-3 parts by weight of the powder.

2. The powder of claim 1 wherein the coloring material includes iron oxide based colors.

3. The powder of claim 2 wherein the coloring material also includes titanium dioxide.

4. The powder of claim 3 wherein the binding agent is at least one compound selected from the group consisting of bismuth oxychloride and magnesium carbonate.

5. The powder of claim 4 wherein said agent is both of said compounds.

6. The powder of claim 5 having the following constituents as expressed in parts by weight:

| CONSTITUENT | PARTS BY WEIGHT |
|---|---|
| TALC | 50.0 |
| MAGNESIUM CARBONATE | 5.0 |
| CRYSTALLINE SILICA | 2.0 |
| MICA | 10.0 |
| TITANIUM DIOXIDE | 2.0 |
| BISMUTH OXYCHLORIDE | 0.5 |
| IRON OXIDE COLORS | 0.5 |

* * * * *